(12) United States Patent
Niddam-Hildesheim et al.

(10) Patent No.: US 7,777,034 B2
(45) Date of Patent: Aug. 17, 2010

(54) CRYSTALLINE AMMONIUM SALTS OF ROSUVASTATIN

(75) Inventors: Valerie Niddam-Hildesheim, Ein Vered (IL); Judith Aronhime, Rehovot (IL); Kobi Chen, Ramat HaSharon (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 793 days.

(21) Appl. No.: 10/996,483

(22) Filed: Nov. 24, 2004

(65) Prior Publication Data

US 2005/0131066 A1    Jun. 16, 2005

Related U.S. Application Data

(60) Provisional application No. 60/525,128, filed on Nov. 24, 2003, provisional application No. 60/534,479, filed on Jan. 5, 2004.

(51) Int. Cl.
C07D 239/42     (2006.01)
A61K 31/505    (2006.01)
A61P 3/06      (2006.01)

(52) U.S. Cl. ................ 544/297; 544/330; 544/332
(58) Field of Classification Search .................. 544/297
See application file for complete search history.

(56) References Cited

U.S. PATENT DOCUMENTS

| | | | |
|---|---|---|---|
| 4,231,938 A | 11/1980 | Monaghan et al. | |
| 4,346,227 A | 8/1982 | Terahara et al. | |
| 4,444,784 A | 4/1984 | Hoffman et al. | |
| 4,739,073 A | 4/1988 | Kathawala | |
| 5,006,530 A | 4/1991 | Angerbauer et al. | |
| 5,177,080 A | 1/1993 | Angerbauer et al. | |
| 5,202,029 A | 4/1993 | Haytko et al. | |
| 5,260,440 A | 11/1993 | Hirai et al. | |
| 5,354,772 A | 10/1994 | Kathawala | |
| 5,354,879 A | 10/1994 | Konoike et al. | |
| RE37,314 E | 8/2001 | Hirai et al. | |
| 6,316,460 B1 | 11/2001 | Creekmore et al. | |
| 6,333,198 B1 | 12/2001 | Edmeades et al. | |
| 6,777,552 B2 | 8/2004 | Niddam-Hildesheim et al. | |
| 6,858,618 B2 | 2/2005 | Raza et al. | |
| 2005/0080134 A1 | 4/2005 | Niddam-Hildesheim et al. | |
| 2005/0131066 A1 | 6/2005 | Niddam-Hildesheim et al. | |
| 2005/0159615 A1 | 7/2005 | Lifshitz-Liron et al. | |
| 2005/0222415 A1 | 10/2005 | Kumar et al. | |
| 2006/0258882 A1 | 11/2006 | Niddam-Hildesheim et al. | |
| 2007/0037979 A1 | 2/2007 | Niddam-Hildesheim et al. | |
| 2007/0179166 A1 | 8/2007 | Niddam-Hildesheim et al. | |

FOREIGN PATENT DOCUMENTS

| | | |
|---|---|---|
| CN | 1 872 841 | 12/2006 |
| EP | 0 065 835 | 11/1985 |
| EP | 0 554 455 | 8/1993 |
| EP | 0 850 902 | 7/1998 |
| EP | 0 521 471 | 10/2000 |
| EP | 1 816 126 | 8/2007 |
| JP | 07 118233 | 5/1995 |
| WO | WO 00/17150 | 3/2000 |
| WO | WO 00/49014 A | 8/2000 |
| WO | WO 01/60804 | 8/2001 |
| WO | WO 03/016317 | 2/2003 |
| WO | WO 03/032995 | 4/2003 |
| WO | WO 03/087112 | 10/2003 |
| WO | WO 03/097614 A | 11/2003 |
| WO | WO 2004/014872 | 2/2004 |
| WO | WO 2004/052867 | 6/2004 |
| WO | WO 2005/021511 | 3/2005 |
| WO | WO 2005/023778 | 3/2005 |
| WO | WO 2005/040134 | 5/2005 |
| WO | WO 2005/077916 | 8/2005 |
| WO | WO 2006/035277 | 4/2006 |
| WO | WO 2006/067456 | 6/2006 |
| WO | WO 2006/079611 | 8/2006 |
| WO | WO 2006/091770 | 8/2006 |
| WO | WO 2006 100689 | 9/2006 |
| WO | WO 2006/106526 | 10/2006 |
| WO | WO 2006/136407 | 12/2006 |
| WO | WO 2006/136408 | 12/2006 |
| WO | WO 2007/007119 | 1/2007 |
| WO | WO 2007/041666 | 4/2007 |
| WO | WO 2007/099561 | 9/2007 |

OTHER PUBLICATIONS

Szantay, et al., "Synthesis of Novel HMG-CoA Reductase Inhibitors, Naphthalene Analogs of Mevinolin", Liebigs Ann. Chem., 1992, pp. 145-157.

Ohrlein, et al., "Chemo-Enzymatic Approach to Statin Side-Chain Building Blocks", Adv. Synth. Catal., 2003, pp. 713-715, vol. 345.

Greene, "Protective Groups in Organic Synthesis", John Wiley & Sons, Inc., 1981.

Tetrahedron, 1997, pp. 10659-10670, vol. 53 (31).

Anelli, et al., "Fast and Selective Oxidation of Primary Alcohols to Aldehydes or to Carboxylic Acids and of Secondary Alcohols to Ketones Mediated by Oxoammonium Salts Under Two-Phase Conditions", J. Org. Chem., 1987, pp. 2559-2562, vol. 52, No. 12.

Hull, et al., "Quantification of Rosuvastatin in Human Plasma by Automated Solid-Phase Extraction Using Tandem Mass Spectrometric Detection", Journal of Chromatography B: Biomedical Sciences & Applications, 2002, pp. 219-228, vol. 772, No. 2.

Konoike, et al. "Practical Synthesis of Chiral Synthons for the Preparation of HMG-CoA Reductase Inhibitors" J. Org. Chem., vol. 59, 1994, pp. 7849-7854.

(Continued)

Primary Examiner—Venkataraman Balasubramanian
(74) Attorney, Agent, or Firm—Kenyon & Kenyon LLP

(57) ABSTRACT

Provided are alkyl ammonium crystalline salts of rosuvastatin that provide for purification of rosuvastatin and its pharmaceutically acceptable salts.

9 Claims, 2 Drawing Sheets

OTHER PUBLICATIONS

Lenz, et al., "Tetra-N-Propylammonium Perruthenate (TPAP)-Catalysed Oxidations of Alcohols Using Molecular Oxygen As a Co-Oxidant", *J. Chem. Soc., Perkin Trans.* 1, 1997, 3291-3292.

Ley, et al., *Synthesis*, 1994, 639-666.

Lipid Research Clinics Program, "The Lipid Research Clinics Coronary Primary Prevention Trial Results: I. Reduction in Incidence of Coronary Heart Disease", *J.A.M.A.*, 1984, 351-74, vol. 251, No. 3.

Scandinavian Simvastatin Survival Study Group, "Randomised Trial of Cholesterol Lowering in 4444 Patients With Coronary Heart Disease: The Scandinavian Survival Study (4s)", *The Lancet*, 1994, pp. 1383-1389, vol. 344.

Snyder, et al., *Introduction to Modern Liquid Chromatography*, 2nd ed., John Wiley & Sons: New York, 1979, pp. 549, 552, 571-572.

Strobel, et al., *Chemical Instrumentation: A Systematic Approach*, 3$^{rd}$ dd., Wiley & Sons: New York, 1989, pp. 391-393, 879, 894, 922, 924-925, 953.

Wantanabe, et al., "Synthesis and Biological Antivity of Methanesulfonamide Pyramidine-And N-Methanesulfonyl Pyrrole-Substituted 3,5-Dihydroxy-6-Heptenoates, a Novel Series of HMG-CoA Reductase Inhibitors", *Bioorganic & Medicinal Chemistry*, 1997, pp. 437-444, vol. 5, No. 2.

Witztum, "Chapter 36: Drugs Used in the Treatment of Hyperlipoproteinemias", *Goodman & Gilman's the Pharmacological Basis of Therapeutics*, 9$^{th}$ ed., pp. 875-897, 1996.

ial Application Nos. 60/525,128 filed on Nov. 24, 2003 and
CRYSTALLINE AMMONIUM SALTS OF ROSUVASTATIN

CROSS-REFERENCE TO RELATED APPLICATIONS

This application claims the benefit of U.S. Provisional Application Nos. 60/525,128 filed on Nov. 24, 2003 and 60/534,479 filed on Jan. 5, 2004, the disclosures of which are incorporated by reference in their entirety herein.

FIELD OF THE INVENTION

The present invention relates to ammonium salts of rosuvastatin.

BACKGROUND OF THE INVENTION

Statins are currently the most therapeutically effective drugs available for reducing low-density lipoprotein (LDL) particle concentration in the blood stream of patients at risk for cardiovascular disease. Thus, statins are used in the treatment of hypercholesterolemia, hyperlipoproteinemia, and atherosclerosis. A high level of LDL in the bloodstream has been linked to the formation of coronary lesions that obstruct the flow of blood and can rupture and promote thrombosis. Goodman and Gilman, The Pharmacological Basis of Therapeutics, page 879 (9th Ed. 1996).

Statins inhibit cholesterol biosynthesis in humans by competitively inhibiting the 3-hydroxy-3-methyl-glutaryl-coenzyme A ("HMG-CoA") reductase enzyme. HMG-CoA reductase catalyzes the conversion of HMG to mevalonate, which is the rate-determining step in the biosynthesis of cholesterol. Decreased production of cholesterol causes an increase in the number of LDL receptors and corresponding reduction in the concentration of LDL particles in the bloodstream. Reduction in the LDL level in the bloodstream reduces the risk of coronary artery disease. J.A.M.A. 1984, 251, 351-74.

Currently available statins include lovastatin, simvastatin, pravastatin, fluvastatin, cerivastatin and atorvastatin. Lovastatin (disclosed in U.S. Pat. No. 4,231,938) and simvastatin (disclosed in U.S. Pat. No. 4,444,784) are administered in the lactone form. After absorption, the lactone ring is opened in the liver by chemical or enzymatic hydrolysis, and the active hydroxy acid is generated. Pravastatin (disclosed in U.S. Pat. No. 4,346,227) is administered as the sodium salt. Fluvastatin (disclosed in U.S. Pat. No. 4,739,073) and cerivastatin (disclosed in U.S. Pat. Nos. 5,006,530 and 5,177,080), also administered as the sodium salt, are entirely synthetic compounds that are in part structurally distinct from the fungal derivatives of this class that contain a hexahydronaphthalene ring. Atorvastatin and two new "superstatins," rosuvastatin and pitavastatin, are administered as calcium salts.

Rosuvastatin calcium (7-[4-(4-fluorophenyl)-6-isopropyl-2-(N-methyl-N-methylsulfonylamino)pyrimidin-5-yl]-(3R,5S)-dihydroxy-(E)-6-heptenoic acid) is an HMG-CoA reductase inhibitor, developed by Shionogi for the once daily oral treatment of hyperlipidaemia (Ann Rep, Shionogi, 1996; Direct communications, Shionogi, 8 Feb. 1999 & 25 Feb. 2000). Rosuvastatin calcium is a so-called superstatin, which can lower LDL-cholesterol and triglycerides more effectively than first generation drugs. Rosuvastatin calcium has the following chemical formula:

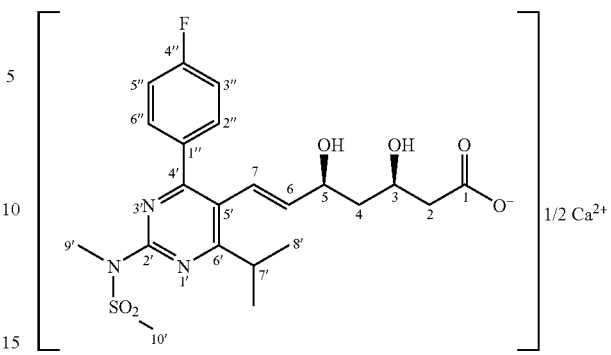

Rosuvastatin calcium is marketed under the name CRESTOR for treatment of a mammal such as a human. According to the maker of CRESTOR, it is administered in a daily dose of from about 5 mg to about 40 mg. For patients requiring less aggressive LDL-C reductions or who have pre-disposing factors for myopathy, the 5 mg dose is recommended, while 10 mg dose is recommended for the average patient, 20 mg dose for patients with marked hyper-cholesterolemia and aggressive lipid targets (>190 mg/dL), and the 40 mg dose for patients who have not been responsive to lower doses.

U.S. Pat. No. 5,260,440 discloses and claims rosuvastatin, its calcium salt (2:1), and its lactone form. The process of the '440 patent prepares rosuvastatin by reacting 4-(4-fluorophenyl)-6-isopropyl-2-(N-methyl-N-methylsulfonylamino)-5-pyrimidinecarbardehyde with methyl(3R)-3-(tert-butyldimethylsilyloxy)-5-oxo-6-triphenylphosphoranylidene hexanate in acetonitrile under reflux. The silyl group is then cleaved with hydrogen fluoride, followed by reduction with $NaBH_4$ to obtain a methyl ester of rosuvastatin.

The ester is then hydrolyzed with sodium hydroxide in ethanol at room temperature, followed by removal of ethanol and addition of ether, to obtain the sodium salt of rosuvastatin. The sodium salt is then converted to the calcium salt with a multi-step process. The sodium salt is dissolved in water and maintained under a nitrogen atmosphere. Calcium chloride is then added to the solution, resulting in precipitation of rosuvastatin calcium (2:1). The process for preparation of the intermediates disclosed in the '440 patent is incorporated herein by reference.

U.S. Pat. No. 6,316,460 discloses a pharmaceutical composition of rosuvastatin. The pharmaceutical compositions contain rosuvastatin or its salt and a multivalent tribasic phosphate salt.

WO 01/60804 discloses various ammonium, lithium and magnesium salts of rosuvastatin.

Even though ammonium salts of rosuvastatin are not likely to be used for administration to a patient, they provide a method for purifying rosuvastatin through crystallization. There is a need in the art for additional salts of rosuvastatin that allow for purification of rosuvastatin through crystallization, particularly since rosuvastatin calcium as marketed under CRESTOR is highly amorphous.

SUMMARY OF THE INVENTION

In one aspect, the present invention provides for crystalline rosuvastatin isopropylammonium salt.

In another aspect, the present invention provides for a crystalline form of rosuvastatin isopropylammonium salt having an X-ray powder diffraction pattern with peaks at 6.2, 18.8, 19.3, 20.6 and 22.3±0.2 deg. 2-theta.

In another aspect, the present invention provides for a process for preparing the above crystalline form of rosuvastatin comprising combining a solution of rosuvastatin acid in an organic solvent with isopropylamine to precipitate the crystalline form and recovering the crystalline form.

In another aspect, the present invention provides for a process for preparing the above crystalline form comprising combining a solution of rosuvastatin acid in acetonitrile or ethyl acetate with isopropylamine followed by stirring at a temperature of about 30° C., followed by cooling to a temperature of less than about 10° C. to precipitate the crystalline form and recovering the crystalline form.

In another aspect, the present invention provides for a process for purifying rosuvastatin calcium comprising
  a) converting rosuvastatin calcium salt to rosuvastatin acid;
  b) converting rosuvastatin acid to the above isopropylammonium salt;
  c) converting the isopropylammonium salt to rosuvastatin calcium.

In another aspect, the present invention provides for a process for purifying rosuvastatin calcium comprising
  a) combining rosuvastatin calcium with water to obtain a mixture;
  b) combining the mixture with an acid to obtain a solution of rosuvastatin acid;
  c) extracting the solution with a water immiscible solvent to obtain an organic phase;
  d) evaporating the organic phase to obtain a residue;
  e) combining the residue with an organic solvent and isopropylamine to obtain the above isopropyl ammonium salt;
  f) cooling the organic solvent to precipitate the isopropyl ammonium salt; and
  g) converting the isopropyl ammonium salt to the calcium salt.

In another aspect, the present invention provides for a crystalline rosuvastatin cyclohexylammonium salt.

In another aspect, the present invention provides for a crystalline form of rosuvastatin cyclohexylammonium salt having an X-ray powder diffraction pattern characterized by peaks at 8.7, 9.5, 15.3, 19.6 and 20.8±0.2 deg. 2-theta.

In another aspect, the present invention provides for a process for preparing the crystalline form of rosuvastatin cyclohexylammonium salt comprising combining a solution of rosuvastatin acid in an organic solvent with cyclohexylamine to precipitate the crystalline form and recovering the crystalline form.

In another aspect, the present invention provides for a process for preparing the above crystalline form comprising combining a solution of rosuvastatin acid in ethyl acetate with cyclohexylamine followed by stirring at a temperature of about 30° C., followed by cooling to a temperature of less than about 10° C. to precipitate the crystalline form and recovering the crystalline form.

In another aspect, the present invention provides for a process for purifying rosuvastatin calcium comprising
  a) converting rosuvastatin calcium salt to rosuvastatin acid;
  b) converting rosuvastatin acid to the above cyclohexylammonium salt;
  c) converting the isopropylammonium salt to rosuvastatin calcium.

In another aspect, the present invention provides for a process for purifying rosuvastatin calcium comprising
  a) combining rosuvastatin calcium with water to obtain a mixture;
  b) combining the mixture with an acid to obtain a solution of rosuvastatin acid;
  c) extracting the solution with a water immiscible solvent to obtain an organic phase;
  d) evaporating the organic phase to obtain a residue;
  e) combining the residue with an organic solvent and the cyclohexylamine to obtain the above cyclohexylamine salt;
  f) cooling the organic solvent to precipitate the cyclohexylammonium salt; and
  g) converting the cyclohexylammonium salt to the calcium salt.

In another aspect, the present invention provides for a process for purifying rosuvastatin calcium comprising
  a) combining rosuvastatin calcium with water to obtain a mixture;
  b) combining the mixture with an acid to obtain a solution of rosuvastatin acid;
  c) extracting the solution with a water immiscible solvent to obtain an organic phase;
  d) evaporating the organic phase to obtain a residue;
  e) combining the residue with an organic solvent and an amine to obtain the ammonium salt;
  f) cooling the organic solvent to precipitate the ammonium salt; and
  g) converting the ammonium salt to the calcium salt.

DETAILED DESCRIPTION OF THE INVENTION

Figure 1:
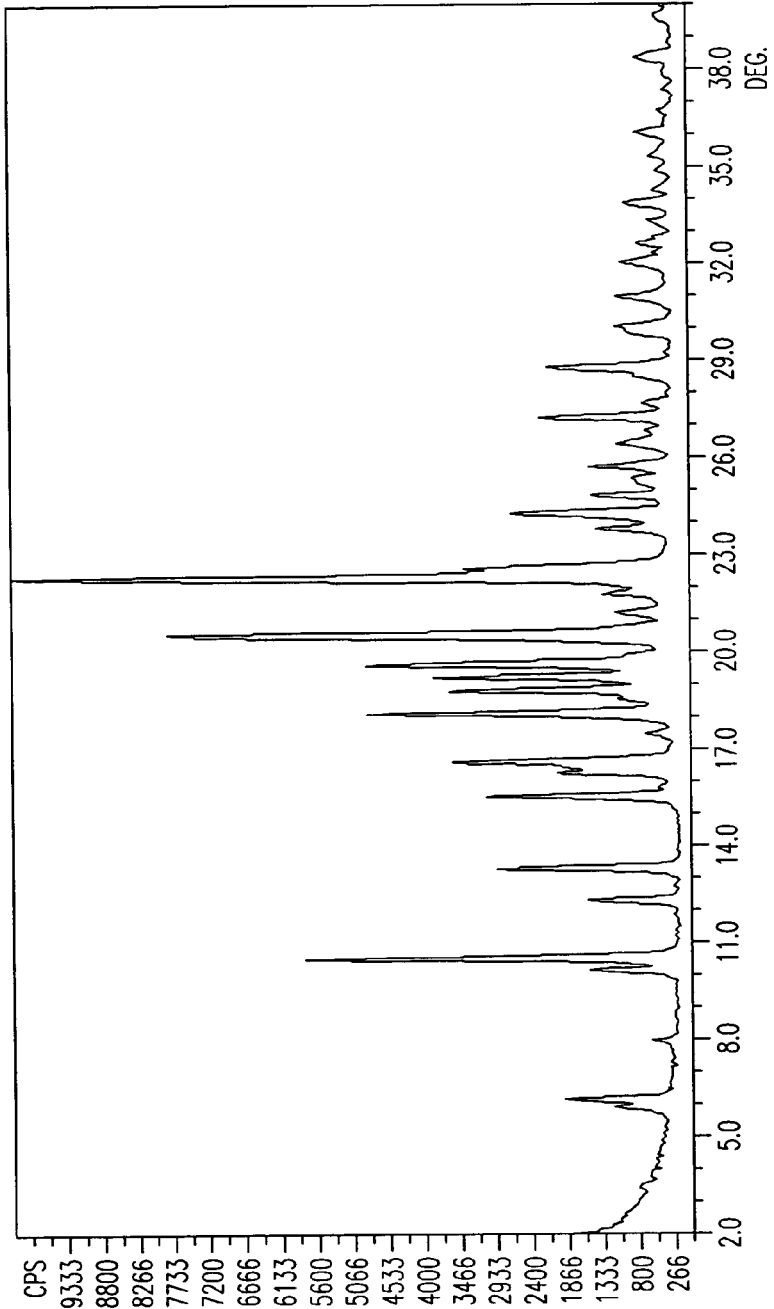
FIG. 1 is an X-ray Powder Diffraction pattern of rosuvastatin isopropylammonium Form A1.

One approach for formulation is to use a crystalline form instead of amorphous form in order to minimize problems generally associated with amorphous form. Another approach for formulation is to purify amorphous form, so that the greater purity imparts additional stability to amorphous form.

An approach to purifying an amorphous active pharmaceutical ingredient ("API") is using a crystalline salt as an intermediate. Crystallization often allows for purification of an API since impurities may be left in the solution after crystallization, or be washed away as insoluble impurities before crystallization. Additional impurities may also be removed by washing the crystals.

The present invention provides crystalline isopropylammonium and cyclohexylammonium salts of rosuvastatin and procedures for their preparation. These salts are useful intermediates for purification of the final product, which is often administered as a calcium salt. The ammonium salt intermediate is particularly useful since it is crystalline, and not highly amorphous like rosuvastatin calcium. For example, the maker of CRESTOR refers to CRESTOR as a white amorphous powder. Amorphous form of an active pharmaceutical ingredient often exhibit lower stability and greater reactivity. Amorphous material may contain impurities, and crystallization as a salt, such as an ammonium salt, allows for purifying the amorphous material.

The purification can start with the calcium salt, followed by its conversion to the acid, which is then converted to the ammonium salt. The ammonium salt may then be converted to a highly pure calcium salt. The purification can also start from other salt or acid forms of rosuvastatin, followed by conversion to the ammonium salt, followed by conversion to the calcium salt. See e.g. WO 04/014872.

The XRD peaks of the two crystalline forms are as follows:

| Typical XRD peaks - deg. 2-theta ± 0.2 (The main characteristic peaks are underlined) | |
|---|---|
| Form A1 | Form B |
| 6.0 | 8.7 |
| 6.2 | 9.5 |
| 10.2 | 10.7 |
| 10.6 | 14.3 |
| 13.4 | 14.7 |
| 15.6 | 15.3 |
| 16.6 | 17.4 |
| 18.2 | 18.0 |
| 18.8 | 19.6 |
| 19.3 | 20.8 |
| 20.6 | 22.1 |
| 22.3 | 28.0 |
| 27.3 | |
| 28.8 | |

The present invention provides crystalline rosuvastatin isopropylammonium salt.

Crystalline rosuvastatin isopropylammonium salt of the present invention (Form A1) has an X-ray powder diffraction pattern (FIG. 1) with principal characteristic peaks at 6.2, 18.8, 19.3, 20.6 and 22.3±0.2 deg. 2-theta. Other characteristic peaks are at 6.0, 10.2, 10.6, 13.4, 15.6, 16.6, 18.2, 27.3 and 28.8±0.2 deg. 2-theta. This Form was previously referred to as Form A in the priority application of the present invention.

Form A1 is generally prepared by combining a solution of rosuvastatin acid in an organic solvent with isopropylamine to precipitate the crystalline form and recovering the crystalline form. After combining, the reaction mixture is preferably stirred at a temperature of about 20° C. to about 40° C., more preferably at a temperature of about 30° C. for a few hours. If precipitation does not occur, the solution is preferably cooled to a temperature of less than about 10° C. Preferably, the solvent is acetonitrile or ethyl acetate.

The present invention provides crystalline form of rosuvastatin cyclohexylammonium salt.

Figure 2:
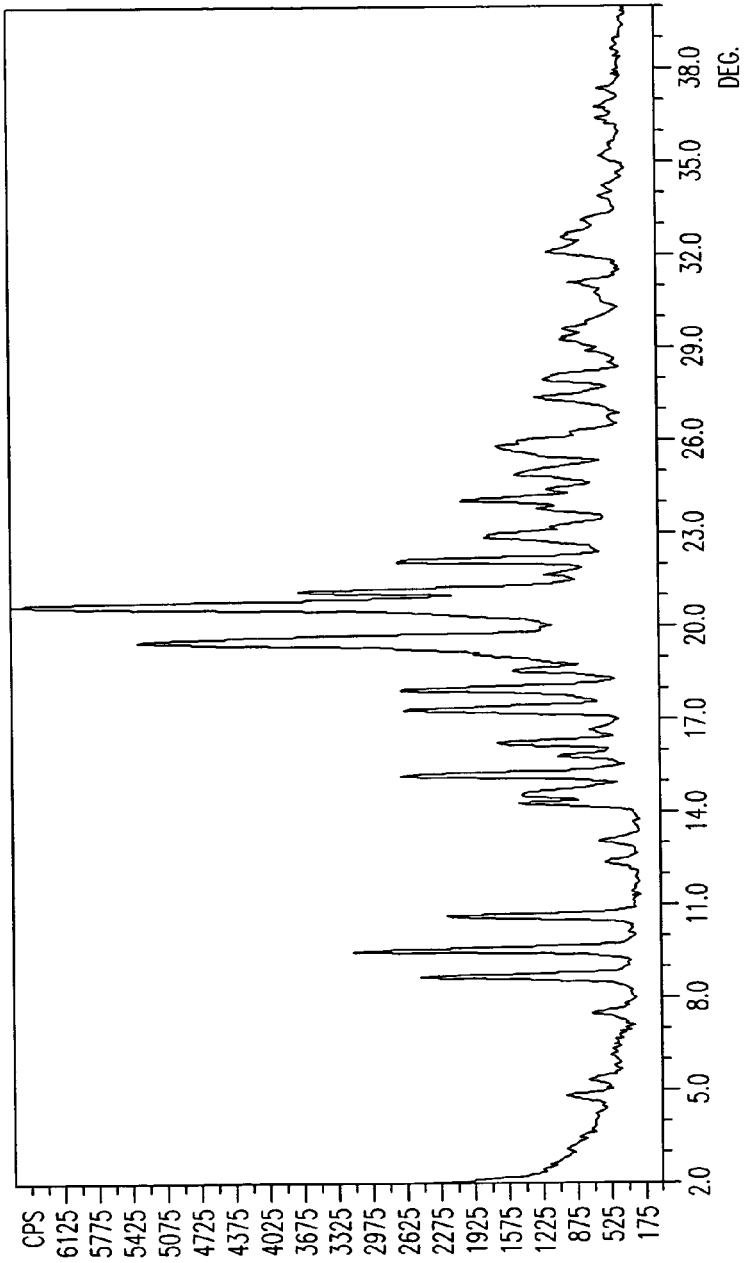
FIG. 2 is an X-ray powder diffraction pattern of rosuvastatin cyclohexylammonium Form B.

Crystalline form of rosuvastatin cyclohexylammonium salt of the present invention (Form B) has an XRPD pattern (FIG. 2) with principal peaks at 8.7, 9.5, 15.3, 19.6 and 20.8±0.2 deg. 2-theta. Other peaks are at 10.7, 14.3, 14.7, 17.4, 18.0, 22.1 and 28.1±0.2 deg. 2-theta.

Form B is generally prepared by combining a solution of rosuvastatin acid in a suitable organic solvent with cyclohexylamine to precipitate the crystalline form and recovering the crystalline form. After combining, the reaction mixture is preferably stirred at a temperature of about 20° C. to about 40° C., more preferably at a temperature of about 30° C. for a few hours. If precipitation does not occur, the solution is preferably cooled to a temperature of less than about 10° C. Preferably, the organic solvent is ethyl acetate.

Form B may be prepared from rosuvastatin calcium as described above in regard to Form A1.

The present invention encompasses embodiments where the amine, rosuvastatin acid/calcium and the organic solvent are added simultaneously, though it is preferred to first obtain a solution of the acid/calcium salt in the solvent.

The above crystalline forms may be recovered by conventional techniques such as filtration, decanting and centrifugation. The resulting salts may optionally be dried to remove residual solvent, such as by drying under reduced pressure (below 1 atmosphere or preferably below about 100 mmHg).

The starting material used in the present invention to obtain the salt is rosuvastatin acid. The acid can be obtained from rosuvastatin calcium. The acid may be isolated and subsequently used, or be used in a one pot procedure where the calcium salt is converted to the amine without isolation of the acid.

In one embodiment, rosuvastatin calcium of amorphous nature is purified by conversion to the acid, which is converted to the above ammonium salts, which is then converted back to amorphous rosuvastatin calcium. The rosuvastatin calcium obtained at the end has a higher purity that the rosuvastatin calcium used as starting material. This scheme can also be used with other pharmaceutically acceptable salts of rosuvastatin which are also amorphous.

In one embodiment, rosuvastatin calcium is combined with water or with a mixture of water and a water-miscible solvent. A preferred mixture is about a 1:2 to about a 2:1 mixture of water and acetonitrile, more preferably a 1:1 mixture (by volume). The weight to volume ratio of the calcium salt is preferably of about 1:10 to about 1:40 Kg/L. The ratio might vary depending on the solvent used, but is of such that a solution would be formed after formation of the acid, and of sufficient concentration to allow for optimal extraction. The acid form may be obtained from the calcium salt by addition of an acid, such as HCl, HBr, or sulfuric acid. After addition of the acid, the reaction mixture may be stirred.

The resulting solution is then extracted with a water immiscible solvent. Preferably, the water immiscible solvent is ethyl acetate. The rosuvastatin acid moves into the organic phase. After extraction, the organic phase may be concentrated, preferably by evaporation at a pressure below about 760 mmHg, more preferably below about 100 mmHg. The temperature can be increased to accelerate the evaporation process. In this embodiment, the resulting residue is then added to an organic solvent, followed by addition of the amine to precipitate the ammonium salt. After the addition, the reaction mixture is preferably stirred at a temperature of about 20° C. to about 40° C., more preferably at a temperature of about 30° C. for a few hours. Preferably, the organic solvent is ethyl acetate. Preferably, the amine is isopropylamine or cyclohexylamine. When the amine is isopropylamine, the ammonium salt is crystalline rosuvastatin isopropylammonium salt form A1. When the amine is cyclohexylamine, the ammonium salt is crystalline rosuvastatin cyclohexylamine salt form B. Precipitation is preferably induced by cooling as described above.

After obtaining the above ammonium salts, the ammonium salts can be converted to rosuvastatin calcium for example by reaction with an aqueous basic solution of sodium or potassium hydroxide (about 8%), followed by reaction with a source of calcium such as calcium chloride or calcium oxide. The calcium salt may be recovered in the solid state by removing the solvent under reduced pressure or by precipitation.

Many processes of the present invention involve crystallization/precipitation out of a particular solvent, i.e., obtaining a solid material from a solution. One skilled in the art would appreciate that the conditions concerning crystallization may be modified without affecting the form of the polymorph obtained. For example, when mixing rosuvastatin in a solvent to form a solution, warming of the mixture may be necessary to completely dissolve the starting material. If warming does not clarify the mixture, the mixture may be diluted or filtered. To filter, the hot mixture may be passed through paper, glass fiber or other membrane material, or a clarifying agent such as celite. Depending upon the equipment used and the concentration and temperature of the solution, the filtration apparatus may need to be preheated to avoid premature crystallization.

The conditions may also be changed to induce precipitation. A preferred way of inducing precipitation is to reduce the solubility of the solvent. The solubility of the solvent may be reduced, for example, by cooling the solvent.

In one embodiment, an anti-solvent is added to a solution to decrease its solubility for a particular compound, thus resulting in precipitation. Another way of accelerating crystallization is by seeding with a crystal of the product or scratching the inner surface of the crystallization vessel with a glass rod. Other times, crystallization may occur spontaneously without any inducement. The present invention encompasses both embodiments where crystallization of a particular form of rosuvastatin occurs spontaneously or is induced/accelerated, unless if such inducement is critical for obtaining a particular form.

Pharmaceutical compositions can be prepared as medicaments to be administered orally, parenterally, rectally, transdermally, bucally, or nasally. Suitable forms for oral administration include tablets, compressed or coated pills, dragees, sachets, hard or gelatin capsules, sub-lingual tablets, syrups and suspensions. Suitable forms of parenteral administration include an aqueous or non-aqueous solution or emulsion, while for rectal administration suitable forms for administration include suppositories with hydrophilic or hydrophobic vehicle. For topical administration the invention provides suitable transdermal delivery systems known in the art, and for nasal delivery there are provided suitable aerosol delivery systems known in the art.

Pharmaceutical formulations of the present invention contain a pharmaceutically acceptable salt of rosuvastatin in the solid state. In addition to the active ingredient(s), the pharmaceutical compositions of the present invention may contain one or more excipients or adjuvants. Selection of excipients and the amounts to use may be readily determined by the formulation scientist based upon experience and consideration of standard procedures and reference works in the field.

Diluents increase the bulk of a solid pharmaceutical composition, and may make a pharmaceutical dosage form containing the composition easier for the patient and care giver to handle. Diluents for solid compositions include, for example, microcrystalline cellulose (e.g. Avicel®), microfine cellulose, lactose, starch, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon dixoide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate. Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In liquid pharmaceutical compositions of the present invention, nateglinide and any other solid excipients are dissolved or suspended in a liquid carrier such as water, vegetable oil, alcohol, polyethylene glycol, propylene glycol or glycerin. Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste. Preservatives and chelating agents such as alcohol, sodium benzoate, butylated hydroxy toluene, butylated hydroxyanisole and ethylenediamine tetraacetic acid may be added at levels safe for ingestion to improve storage stability.

According to the present invention, a liquid composition may also contain a buffer such as guconic acid, lactic acid, citric acid or acetic acid, sodium guconate, sodium lactate, sodium citrate or sodium acetate.

Selection of excipients and the amounts used may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and losenges, as well as liquid syrups, suspensions and elixirs.

The dosage form of the present invention may be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

The active ingredient and excipients may be formulated into compositions and dosage forms according to methods known in the art.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

Preferred dosage is from about 5 mg to about 80 mg per day, more preferably about 5 mg to about 40 mg per day, with 5 mg, 10 mg, 20 mg, 40 mg and 80 mg tablets for once a day being preferred. These tablets may have the following inactive ingredients: microcrystalline cellulose NF, lactose monohydrate NF, tribasic calcium phosphate NF, crospovidone NF, magnesium stearate NF, hypromellose NF, triacetin NF and titanium dioxide USP.

Also provided are formulations of highly pure calcium salt of rosuvastatin and its methods of administration.

X-Ray powder diffraction data were obtained by conventional methods using a SCINTAG powder X-Ray diffractometer model X'TRA equipped with a solid state detector. Copper radiation of 1.5418 lambda was used. A round aluminum sample holder with zero background was used. All peak positions are within 0.2 degrees two theta.

Procedures

Example 1

Preparation of Rosuvastatin iso-Propylammonium Salt in ACN

A 100 ml three necked flask equipped with a mechanical stirrer was charged with rosuvastatin Ca salt (3 g), water (30 ml) and acetonitrile (30 ml).

6 ml of HCl 1N was added portion-wise at room temperature. The mixture was stirred at room temperature for 1 hour. The clear solution was then extracted with 3 portions of 20 ml ethyl acetate. The organic phase was concentrated under reduced pressure of 10-100 mm Hg at 45° C. to obtain a residue (4 g), which contains rosuvastatin acid.

Acetonitrile (30 mL) was added to the residue, the solution was stirred at room temperature for 5 minutes. 0.36 g of iso-propylamine were added dropwise and the solution was stirred at 30° C. for 90 minutes, then cooled at 0°-2° C. (ice-water bath), and stirred for 2 hours. The iso-propylammonium salt was collected by filtration under reduced pressure to obtain white crystals. (1.6 g, 49.4%) in crystal form A1.

Example 2

Preparation of Rosuvastatin iso-Propylammonium Salt in Ethyl Acetate

A 100 ml three necked flask equipped with a mechanical stirrer was charged with rosuvastatin Ca salt (3 g), water (30 ml) and acetonitrile (30 ml).

6 ml of HCl 1N was added portion-wise at room temperature. The mixture was stirred at room temperature for 1 hour. The clear solution was then extracted with 3 portions of 20 ml ethyl acetate. 6 g of anhydrous $Na_2SO_4$ was added to the organic phase, the mixture was then stirred for 5 minutes, filtered and concentrated under reduced pressure of 10-100 mm Hg at 45° C. to obtain a residue (4 g) which contains rosuvastatin acid.

15 ml of Ethyl acetate was added to the residue, the solution was stirred at room temperature for 5 minutes. 0.36 g of iso-propylamine were added dropwise and the solution was stirred at 30° C. for 90 minutes, then cooled at 0°-2° C. (ice-water bath) and stirred for 2 hours. The iso-propylammonium salt was collected by filtration under reduced pressure and washed with 10 ml of ehyl acetate to obtain white crystals. (2.0 g, 61.7%) in crystal form A1.

Example 3

Same as Example 2 Except the Preparation of the Rosuvastatin Acid

A 100 ml three necked flask equipped with a mechanical stirrer was charged with rosuvastatin ca salt (3 g) and water (30 ml). 6 ml of HCl 1N was added portion-wise at room temperature. The mixture was stirred at room temperature for 1 hour. 20 ml of Ethyl acetate was added while stirring for 10 minutes to obtain a clear solution. The phases were separated, the aqueous phase was then extracted with 2 portions of 20 ml ethyl acetate. 6 g of anhydrous $Na_2SO_4$ was added to the organic phase, the mixture was then stirred for 5 minutes, filtered and concentrated under reduced pressure of 10-100 mm Hg at 45° C. to obtain a residue (4 g) which contains rosuvastatin acid.

15 ml of ethyl acetate was added to the residue, the solution was stirred at room temperature for 5 minutes. 0.36 g of iso-propylamine were added dropwise and the solution was stirred at 30° C. for 90 minutes, then cooled at 0°-2° C. (ice-water bath) and stirred for 2 hours. The iso-propylammonium salt was collected by filtration under reduced pressure and washed with 10 ml of ethyl acetate to obtain white crystals (2.5 g, 77.2%) in crystal form A1.

Example 4

Preparation of Rosuvastatin Cyclohexylammonium Salt (ROSU-CHA) in Ethyl Acetate A 100 ml three necked flask equipped with a mechanical stirrer was charged with rosuvastatin Ca salt (3 g), water (30 ml) and acetonitrile (30 ml). 6 ml of HCl 1N was added portion-wise at room temperature. The mixture was stirred at room temperature for 1 hour. The clear solution was then extracted with 3 portions of 20 ml ethyl acetate. 6 g of anhydrous $Na_2SO_4$ was added to the organic phase, the mixture was then stirred for 5 minutes, filtered and concentrated under reduced pressure of 10-100 mm Hg at 45° C. to obtain a residue (4 g) which contains rosuvastatin acid. 15 ml of ethyl acetate was added to the residue, the solution was stirred at room temperature for 5 minutes. 0.75 ml of cyclohexylamine were added dropwise and the solution was stirred at 30° C. for 90 minutes, then cooled at 0°-2° C. (ice-water bath) and stirred for 2 hours. The Rosu-CHA salt was collected by filtration under reduced pressure and washed with 10 ml of Ethyl acetate to obtain white crystals (2.9 g, 83.5%) in crystal form B.

Example 5

Purification of Rosuvastatin Calcium by Using iso-Propylammonium Salt as an Intermediate A 100 ml three necked flask equipped with a mechanical stirrer was charged with Rosuvastatin Ca salt (3 g) and water (30 ml). HCl 1N (6 ml) was added portion-wise at room temperature. The mixture was stirred at room temperature for 1 hour. Ethyl acetate (20 ml) was added, while stirring for 10 minutes to obtain a clear solution. The phases were separated. The aqueous phase was then extracted with 2 portions of ethyl acetate (20 ml). Anhydrous $Na_2SO_4$ (6 g) was added to the organic phase. The mixture was then stirred for 5 minutes, filtered and concentrated under reduced pressure at 45° C. to obtain a residue (4 g) which contained Rosuvastatin acid. Ethyl acetate (15 ml) was added to the residue, the solution was stirred at room temperature for 5 minutes. Iso-Propylamine (0.36 g) was added dropwise to the solution, and the solution was stirred at 30° C. for 90 minutes. The resulting mixture was cooled at 0°-2° C. (ice-water bath) and stirred for 2 hours. The iso-Propylammonium salt was collected by filtration under reduced pressure and washed with ethyl acetate (10 ml) to obtain white crystals (2.5 g, 77.2%) in crystal form A1. A 100 ml three necked flask equipped with a mechanical stirrer was charged at ambient temperature with rosuvastatin iso-Propylammonium salt (2.2 grams) generally prepared according to the above procedure. Water (30 ml), ethanol (22 ml) and sodium hydroxide (0.2 g). The reaction mixture was stirred for 2 hours and the clear solution was filtered under reduced pressure. The mixture was concentrated under reduced pressure at 50° C. to obtain a residue. Then water (22 ml) was added and the aqueous phase was washed with EtOAc (2×10 ml). Traces of EtOAc in the aqueous phase were distilled off under reduced pressure at 50° C. Make-up of water was done (10 ml) at the end of the evaporation. To this solution $CaCl_2$ (0.45 g) was added. The reaction mixture was then stirred at ambient temperature for 2 hours, filtered and washed to get 1.5 g (73.6%) of Rosuvastatin calcium.

Having thus described the invention with reference to particular preferred embodiments and illustrated it with Examples, those in the art can appreciate modifications to the invention as described and illustrated that do not depart from the spirit and scope of the invention as disclosed in the specification. The Examples are set forth to aid in understanding the invention but are not intended to, and should not be construed to, limit its scope in any way. The examples do not include detailed descriptions of conventional methods.

What is claimed is:

1. A crystalline form of rosuvastatin isopropylammonium salt having an X-ray powder diffraction pattern with peaks at 6.2, 18.8, 19.3, 20.6 and 22.3±0.2 deg. 2-theta.

2. The crystalline form of claim 1, further having peaks at 6.0, 10.2, 10.6, 13.4, 15.6, 16.6, 18.2, 27.3 and 28.8±0.2 deg. 2-theta.

3. The crystalline form of claim 1, wherein the crystalline form has an X-ray powder diffraction pattern substantially as depicted in FIG. 1.

4. A process for preparing the crystalline form of claim 1, said process comprising combining a solution of rosuvastatin acid in an organic solvent with isopropylamine to precipitate the crystalline form and recovering the crystalline form.

5. The process of claim 4, wherein precipitation is induced by cooling the solution to a temperature of less than about 10° C.

6. The process of claim 4, wherein the combining is at a temperature of about 20° C. to about 40° C.

7. The process of claim 6, wherein the temperature is about 30° C.

8. The process of claim 4, wherein the solvent is acetonitrile or ethyl acetate.

9. A process for preparing the crystalline form of claim 1, said process comprising combining a solution of rosuvastatin acid in acetonitrile or ethyl acetate with isopropylamine followed by stirring at a temperature of about 30° C., followed by cooling to a temperature of less than about 10° C. to precipitate the crystalline form and recovering the crystalline form.

* * * * *

UNITED STATES PATENT AND TRADEMARK OFFICE
CERTIFICATE OF CORRECTION

PATENT NO. : 7,777,034 B2
APPLICATION NO. : 10/996483
DATED : August 17, 2010
INVENTOR(S) : Niddam-Hildesheim et al.

It is certified that error appears in the above-identified patent and that said Letters Patent is hereby corrected as shown below:

On the Cover of the patent, # (75) Inventors, line 1, change "Ein Vered" to -- Kadima --

On the Cover of the patent, # (75) Inventors, line 3, change "Ramat HaSharon" to -- Kfar-Saba --

Signed and Sealed this
Thirteenth Day of September, 2011

David J. Kappos
*Director of the United States Patent and Trademark Office*